(12) United States Patent
Qi et al.

(10) Patent No.: US 10,639,289 B2
(45) Date of Patent: May 5, 2020

(54) APPLICATION OF NEURAMINIDASE AND INHIBITORS THEREOF IN MYOCARDIAL ISCHEMIA AND MYOCARDIAL INFARCTION

(71) Applicant: CHINA PHARMACEUTICAL UNIVERSITY, Nanjing (CN)

(72) Inventors: Lianwen Qi, Nanjing (CN); Lei Zhang, Nanjing (CN); Tingting Wei, Nanjing (CN); Yong Fan, Nanjing (CN)

(73) Assignee: CHINA PHARMACEUTICAL UNIVERSITY, Nanjing (CN)

( * ) Notice: Subject to any disclaimer, the term of this patent is extended or adjusted under 35 U.S.C. 154(b) by 0 days.

(21) Appl. No.: 16/081,436

(22) PCT Filed: Mar. 29, 2016

(86) PCT No.: PCT/CN2016/077605
§ 371 (c)(1),
(2) Date: Aug. 31, 2018

(87) PCT Pub. No.: WO2017/161594
PCT Pub. Date: Sep. 28, 2017

(65) Prior Publication Data
US 2019/0054055 A1 Feb. 21, 2019

(30) Foreign Application Priority Data
Mar. 22, 2016 (CN) .......................... 2016 1 0166253

(51) Int. Cl.
| | |
|---|---|
| *A61K 31/215* | (2006.01) |
| *A61K 38/47* | (2006.01) |
| *A61K 31/351* | (2006.01) |
| *A61K 31/4375* | (2006.01) |
| *A61K 31/7012* | (2006.01) |
| *A61K 31/437* | (2006.01) |
| *A61P 9/10* | (2006.01) |

(52) U.S. Cl.
CPC .......... *A61K 31/215* (2013.01); *A61K 31/351* (2013.01); *A61K 31/437* (2013.01); *A61K 31/4375* (2013.01); *A61K 31/7012* (2013.01); *A61K 38/47* (2013.01); *A61P 9/10* (2018.01)

(58) Field of Classification Search
CPC ....... A61P 9/10; A61K 31/215; A61K 31/351; A61K 31/437; A61K 31/4375; A61K 31/7012; A61K 38/47
USPC ...................................................... 424/94.61
See application file for complete search history.

(56) References Cited

FOREIGN PATENT DOCUMENTS

| | | | |
|---|---|---|---|
| CN | 101886097 A | | 11/2010 |
| CN | 102000073 | * | 4/2011 |
| CN | 102000073 A | | 4/2011 |
| CN | 104857007 A | | 8/2015 |
| WO | 2010102112 A2 | | 9/2010 |

OTHER PUBLICATIONS

Golabchi et al., What Every Cardiologist Should Know About H1N 1?, Arya Atherosclerosis Journal, 6(3), (2010) p. 118-121.*

* cited by examiner

*Primary Examiner* — Jennifer M. H. Tichy
(74) *Attorney, Agent, or Firm* — Bayramoglu Law Offices LLC

(57) ABSTRACT

The present invention discloses an application of neuraminidase and inhibitors thereof in myocardial ischemia and myocardial infarction, provides a correlation between neuraminidase and myocardial ischemic damage to prove the myocardial ischemic damage can be alleviated by inhibiting the activity of neuraminidase, and to prove the neuraminidase can be used as a target for screening drugs for preventing, alleviating and/or treating myocardial ischemic damage. The present invention also demonstrates the alleviating effect of neuraminidase inhibitors on myocardial ischemic damage. Neuraminidase inhibitors improves myocardial ischemic damage by reducing the level of neuraminidase. The present invention further provides a pharmaceutical preparation comprising neuraminidase inhibitor(s) and pharmaceutically acceptable carrier(s), the pharmaceutical preparation can be used for reducing the level of neuraminidase, thus improving myocardial ischemic damage.

1 Claim, 4 Drawing Sheets

APPLICATION OF NEURAMINIDASE AND INHIBITORS THEREOF IN MYOCARDIAL ISCHEMIA AND MYOCARDIAL INFARCTION

CROSS REFERENCE TO RELATED APPLICATIONS

This application is the national phase entry of International Application No. PCT/CN2016/077605, filed on Mar. 29, 2016, which is based upon and claims priority to Chinese Patent Application No. 201610166253.5, filed on Mar. 22, 2016; the entire contents of which are incorporated herein by reference.

TECHNICAL FIELD

The present invention belongs to the biomedicine field and relates to the discovery and application of drug targets, in particular, to the application of neuraminidase and its inhibitors in myocardial ischemia and myocardial infarction.

BACKGROUND

Cardiovascular disease is a major disease that threatens human life and health. As society progresses and people's living standards improve, its incidence increases year by year. In 2014, the number of deaths resulted from cardiovascular disease accounted for about 30% of the total global death toll, and myocardial ischemic disease is the focus of cardiovascular disease and can develop into arrhythmia, myocardial infarction, and often life-threatening. Therefore, how to practically and effectively reduce the damage caused by myocardial ischemia has become a hot topic in the medical field.

Myocardial ischemic damage is the result of myocardial cell necrosis or impaired function caused by cardiomyocyte hypoxia. The most commonly used drugs in the clinic nowadays are to treat myocardial ischemia by improving cellular energy metabolism, inhibiting inflammatory response, protecting blood vessels, and alleviating calcium overload in cardiomyocytes and the most commonly used drugs include nitrates such as nitroglycerin, isosorbide dinitrate; beta-blockers such as propranolol; calcium channel blockers such as nifedipine and verapamil as well as antiplatelet and antithrombotic drugs such as dipyridamole.

Neuraminidase (NA) is a glycoprotein on the surface of influenza virus with exoglycosidase activity that cleaves α-glycosidic bonds between cell surface sialic acid and adjacent lactose. During the entire life cycle of influenza virus, NA plays a role in recognizing receptors for influenza virus-infected cells and promoting virus' entry into recipient cells. This process plays a key role in viral infection and transmission. Therefore, neuraminidase is an important target for the development of anti-influenza drugs. The currently used neuraminidase inhibitors, zanamivir and oseltamivir phosphate, play an important role in the prevention and treatment of influenza.

SUMMARY

The first goal of the present invention is to provide an application of neuraminidase as a drug target for screening of drugs for preventing, alleviating and/or treating myocardial ischemic damage;

The second goal of the present invention is to provide an application of neuraminidase inhibitor(s) in the preparation of drugs for preventing, alleviating and/or treating myocardial ischemic damage;

The third goal of the present invention is to provide a pharmaceutical preparation comprising neuraminidase inhibitor(s) and pharmaceutically acceptable carrier(s).

The above goals of the present invention are achieved by the following technical solutions:

The application of neuraminidase as a drug target in screening of drugs for preventing, alleviating and/or treating myocardial ischemic damage.

Further, said myocardial ischemia is myocardial ischemia caused by myocardial infarction.

The application of neuraminidase inhibitor(s) in the preparation of drugs for preventing, alleviating and/or treating myocardial ischemic damage.

The application of a pharmaceutical preparation for preventing, alleviating and/or treating myocardial ischemic damage, which includes neuraminidase inhibitor(s) and pharmaceutically acceptable carrier(s).

Further, based on the said application of a pharmaceutical preparation for preventing, alleviating and/or treating myocardial ischemic damage, the neuraminidase inhibitor is zanamivir.

Further, based on the said application of a pharmaceutical preparation for preventing, alleviating and/or treating myocardial ischemic damage, the neuraminidase inhibitor is oseltamivir phosphate.

Further, based on the said application of a pharmaceutical preparation for preventing, alleviating and/or treating myocardial ischemic damage, the neuraminidase inhibitor is coptisine.

Further, based on the said application of a pharmaceutical preparation for preventing, alleviating and/or treating myocardial ischemic damage, the neuraminidase inhibitor is combination of zanamivir and coptisine.

Further, based on the said application of a pharmaceutical preparation for preventing, alleviating and/or treating myocardial ischemic damage, the neuraminidase inhibitor is combination of oseltamivir phosphate and coptisine.

Further, based on the said application of a pharmaceutical preparation for preventing, alleviating and/or treating myocardial ischemic damage, the myocardial ischemia is myocardial ischemia caused by myocardial infarction.

Advantages of the Invention

1. The present invention provides a correlation between neuraminidase and myocardial ischemic damage, and proves that myocardial ischemic damage can be alleviated by inhibiting the activity of neuraminidase, and that neuraminidase can be used as a target for screening drugs for preventing, alleviating and/or treating myocardial ischemic damage;

2. The present invention demonstrates the alleviation of neuraminidase inhibitor(s) on myocardial ischemic damage, and neuraminidase inhibitor(s) improve myocardial ischemic damage by reducing the level of neuraminidase;

3. The present invention provides a pharmaceutical preparation comprising neuraminidase inhibitor(s) and pharmaceutically acceptable carrier(s), which can be used to reduce the level of neuraminidase and thereby improve myocardial ischemic damage.

DETAILED DESCRIPTION OF THE EMBODIMENTS

Figure 1A:
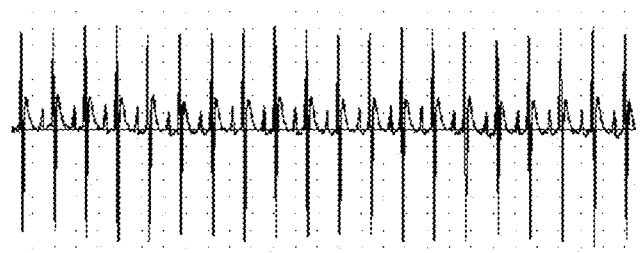
FIG. 1A is the electrocardiogram of a blank rate control group.

The substantial content of the present invention is further illustrated by the following embodiments, but it is not intended to limit the scope of the protection for the present invention. While the present invention has been described in detail with reference to the preferred embodiments, it is understood that it may be modified or equivalently substituted by one of ordinary skill in the art without departing from the spirit and scope of the invention. The test materials or test methods which are not described in detail or specifically emphasized in the present invention are conventional test materials or test methods in the art, and those skilled in the art can obtain the test materials or have the ability to carry out the test.

Embodiment 1: Improvement of Myocardial Ischemic Damage by Neuraminidase Inhibitors, Zanamivir and Oseltamivir Phosphate I. Test Materials 1. Instruments and Reagents Physiological recorders: BL-420S physiological function system (China Chengdu Taimeng), animal ventilator HX-300S (China Chengdu Taimeng), MP120-1 electronic scale (Shanghai Second Balance Instrument Plant), animal surgical instruments, etc.

Isoproterenol hydrochloride (ISO) are purchased from Shanghai Aladdin Biochemical Technology Co., Ltd., purity >99%; 0.9% saline are purchased from Sinopharm Group, and zanamivir (ZA) are purchased from Dalian Meilun Biotechnology Co., Ltd., purity 98?; oseltamivir phosphate (OS) are purchased from Dalian Meilun Biotechnology Co., Ltd., purity 98%; 3% chloral hydrate.

2. Test Animals

120 SD male rats were purchased from B&K Universal Group Limited.

II. Test Method

1. The acute myocardial ischemia model in rats with ISO: SD rats are selected and divided according to body weight into six groups: blank control group, model group, ZA high dose group (0.5 mg/kg iv) and ZA low dose group (0.2 mg/kg iv), OS high dose group (10 mg/kg po), OS low dose group (5 mg/kg po), with 10 rats in each group. The groups with drug administration are administered the drugs continuously for 3 days, and on the second day of drug administration, and 30 minutes after the drug administration, they are performed subcutaneous injection of ISO at a dose of 60 mg/kg; on the third day of drug administration, and 30 minutes after the drug administration, they are also performed subcutaneous injection of ISO at a dose of 60 mg/kg; on the fourth day their tissue samples such as blood and heart are collected on the fourth day.

2. The acute myocardial ischemia model in rats with left anterior descending coronary artery ligation: SD rats are selected and divided into 6 groups according to body weight: blank control group, model group, ZA high dose group (0.5 mg/kg iv). ZA low dose group, (0.2 mg/kg iv), OS high-dose group (10 mg/kg po) and OS low-dose group (5 mg/kg po), with 10 rats in each group. The groups with drug administration are pre-administered drugs 24 h and 12 h in advance before the rats are anesthetized with 3% chloral hydrate at 10 ml/kg, laid flat on their backs and fixed on the rat plate. Then cut them open at between left 4th and 5th ribs to open the pericardium, expose the heart, gently press the thorax to extrude the heart, find the left anterior descending coronary artery in the pulmonary artery cone and left atrium, and immediately bind the root of the left anterior descending coronary artery (pulmonary artery cone and left atrial appendage) with suture 0; push the heart back to the chest, and squeeze out the blood and gas in the chest cavity, close the chest cavity quickly, suture the skin, and the chest opening time is no more than 30 s. Use the BL-420S physiological function test system to perform electrocardiogram on each rat. Collect blood samples such as blood and heart 24 hours after model is established; take out the eyeballs to collect blood, separate serum, and store them at −20° C. for testing; sacrifice the animals by severing cervical vertebrae, quickly remove the heart, and use ice physiological saline to wash off residual blood, remove large blood vessels and connective tissues, and use filter paper to blot them dry before weighing the whole hearts. Take the apical portion of the hearts and fix it in 10% formalin solution for pathological examination. Then crush the rest of the hearts, make them into 10% heart homogenate in an ice bath with 10× Tris-HCl (pH 7.4) buffer; centrifuge the homogenate at 1000 g for 10 min at 4° C., discard the precipitate, and take the supernatant for detection of various enzyme indexes.

3. Observation Indicators and Methods 3.1 Record the Electrocardiogram

Record the electrocardiogram of each group using standard II lead 3.2 Observe the Cardiac Pathology Fix the myocardial tissue of the apical site of the hearts in 10% formaldehyde solution, obtain material conventionally, perform dehydration, embedding in paraffin, and make it into sheets (4 μm thick), stain them with HE, and observe them under an optical microscope.

3.3 Determination of Myocardial Neuraminidase Level

The level of myocardial neuraminidase in the rat is detected by ELBA, and the detection kit is a neuraminidase detection kit, which is measured according to the instruction manual of the test kit.

3.4 the Detection Method for Serum Myocardial Damage Indicator CK-MB and D-LDH

Measure CK-MB and D-LDH according to the CK-MB detection kit (Roche) and D-LDH detection kit (Invitrogen) operating instructions, respectively.

III. The Test Results

1. Impact on the ECG

Figure 1B:
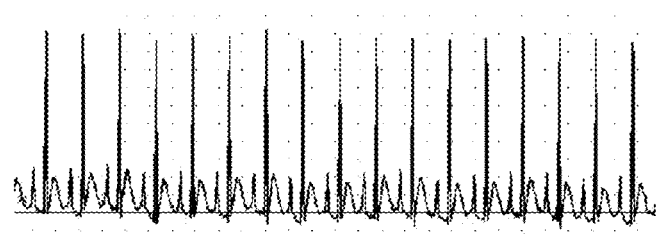
FIG. 1B is the electrocardiogram of a rat model group after isoproterenol modeling.
Figure 2A:
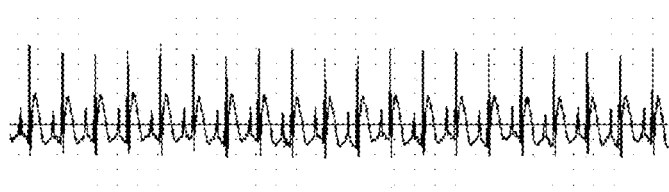
FIG. 2A is the electrocardiogram of the low zanamivir dose rat group after isoproterenol modeling.
Figure 2B:
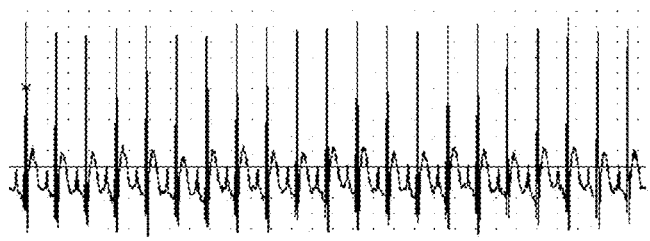
FIG. 2B is the electrocardiogram of the high zanamivir dose rat group after isoproterenol modeling.
Figure 3A:
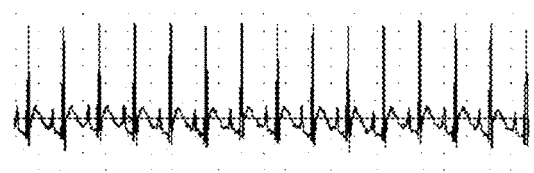
FIG. 3A is the electrocardiogram of the low oseltamivir phosphate dose rat group after oseltamivir phosphate modeling.
Figure 3B:
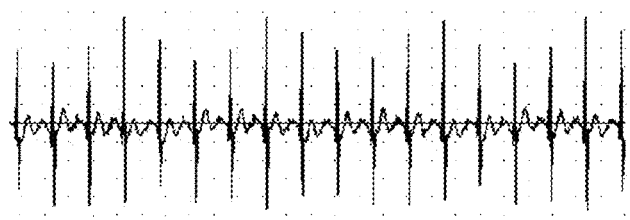
FIG. 3B is the electrocardiogram of the high oseltamivir phosphate dose rat group after oseltamivir phosphate modeling.

The typical electrocardiogram records shown in FIGS. 1 to 3 show that after isoproterenol modeling, the model group has showed significant myocardial damage, and the neuraminidase inhibitors zanamivir and oseltamivir can effectively improve myocardial damage in a dose-dependent manner.

2. Effect on Myocardial Cell Morphology

Figure 4A:
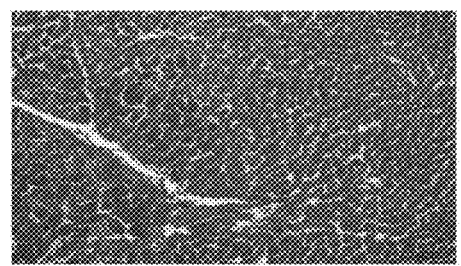
FIG. 4A is the electrocardiogram of cardiac pathology of a blank rate control group.
Figure 4B:
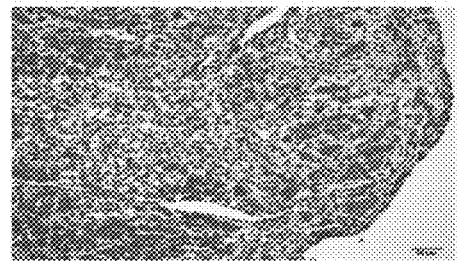
FIG. 4B is the electrocardiogram of cardiac pathology of a rat model group after isoproterenol modeling.
Figure 5A:
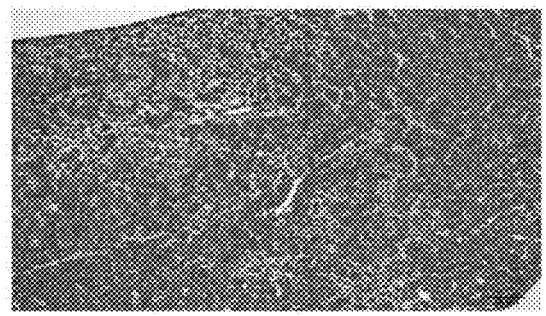
FIG. 5A is the electrocardiogram of cardiac pathology for the low zanamivir dose group after isoproterenol modeling.
Figure 5B:
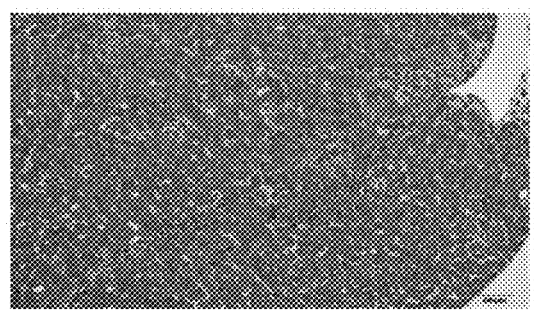
FIG. 5B is the electrocardiogram of cardiac pathology for the high zanamivir dose group after isoproterenol modeling.
Figure 6A:
FIG. 6A is the electrocardiogram of cardiac pathology for the low oseltamivir phosphate dose group after isoproterenol modeling.
Figure 6B:
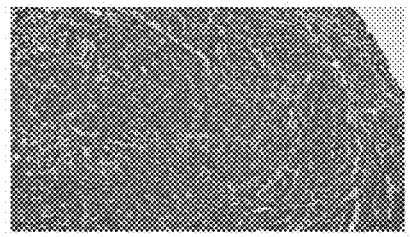
FIG. 6B is the electrocardiogram of cardiac pathology for the high oseltamivir phosphate dose group after isoproterenol modeling.

The typical cardiac pathological sections shown in FIGS. 4 to 6 show that after isoproterenol modeling, the model group has showed obvious myocardial damage, which are manifested as irregular morphology of cardiomyocytes, obvious intercellular fissures, infiltration of a large number of inflammatory cells, and neuraminidase inhibitors zanamivir and oseltamivir were effective in improving myocardial damage in a dose-dependent manner.

3. Effect on the Expression Level of Myocardial Neuraminidase

Figure 7:
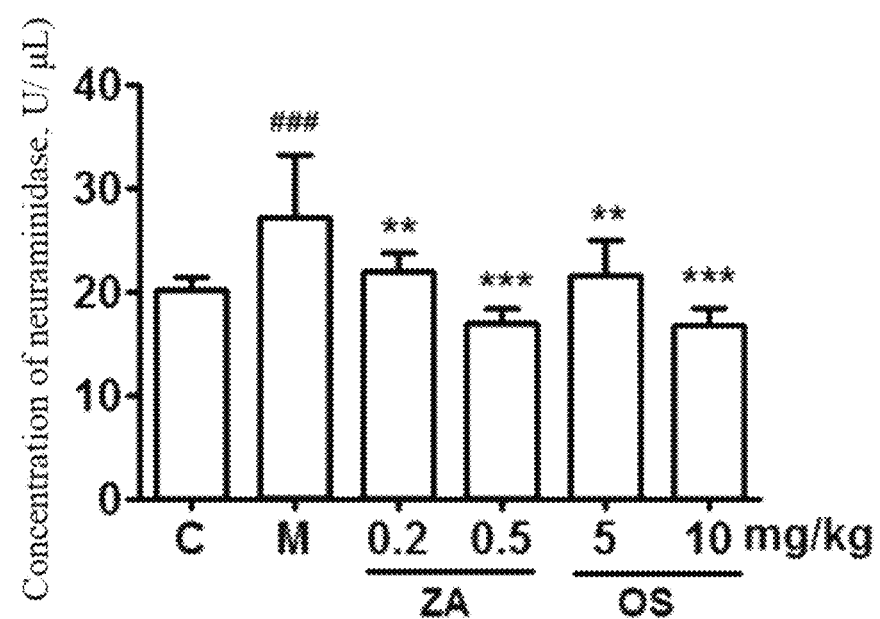
FIG. 7 shows the effect on myocardial neuraminidase expression levels in each group after isoproterenol modeling.

Table 1 and FIG. 7 show that after isoproterenol modeling, the expression of neuraminidase in rat cardiomyocytes is tested by ELISA. The results show that the expression of neuraminidase has been increased after myocardial ischemia in the model group. The neuraminidase inhibitors zanamivir and oseltamivir are effective in inhibiting the increase in neuraminidase expression induced by myocardial ischemia in a dose-dependent manner.

TABLE 1

Myocardial neuraminidase expression levels in each group

| Group | | Neuraminidase concentration (U/μL) |
|---|---|---|
| Blank control group | | 20.1167 |
| Model group | | 27.1509 |
| Zanamivir group | Low dose group | 21.8341 |
| | High dose group | 16.9244 |
| Oseltamivir phosphate group | Low dose group | 21.547 |
| | High dose group | 16.7202 |

4. Effect of Myocardial Damage Index on Serum Expression Level

CK-MB and D-LDH are serum markers of myocardial ischemic damage. After isoproterenol-induced acute myocardial ischemia, serum CK-MB and LDH levels increased, while that in the drug-administered groups decreased significantly. The results are shown in Table 2.

TABLE 2

Serum CK-MB, D-LDH expression levels

| Group | | CK-MB concentration | D-LDH concentration (mU/ml) |
|---|---|---|---|
| Blank control group | | 2734.78 | 6.60748 |
| Model group | | 4607.51 | 9.38718 |
| Zanamivir group | Low dose group | 3713.33 | 8.80382 |
| | High dose group | 3544.44 | 8.38312 |
| Oseltamivir phosphate group | Low dose group | 2964.44 | 7.79294 |
| | High dose group | 2846.67 | 7.20812 |

In the left anterior descending coronary artery ligation model in rats, we have obtained a similar conclusion to that of the isoproterenol-induced acute myocardial ischemia model. In the coronary artery ligation model group, the myocardial neuraminidase activity is increased, so is serum CK-MB and LDH level, which is significantly decreased in the drug-administered groups. At the same time, zanamivir and oseltamivir significantly improve electrocardiogram and cardiac pathology in rats.

Embodiment 2: Coptisine's Inhibition Effect on Neuraminidase and its Improvement Effect on Myocardial Ischemic Damage I. Test Materials 1. Instruments and Reagents Coptisine are purchased from Sichuan Weikeqi Biotechnology Co., Ltd., purity >98%; other instruments and reagents are the same as in Embodiment 1.

2. Test Animals 100 rats, the same source as in Embodiment 1.

II. Test Method

1. The acute myocardial ischemia model in rats with ISO: SD rats are selected and divided according to body weight into five groups: blank control group, model group, coptisine high dose group (100 mg/kg p.o.) and coptisine medium dose group 25 mg/kg p.o.), coptisine low dose group (10 mg/kg p.o.), with 10 rats in each group. The groups with drug administration are administered the drugs continuously for 3 days, and on the second day of drug administration, and 30 minutes after the drug administration, they are performed subcutaneous injection of ISO at a dose of 60 mg/kg; on the third day of drug administration, and 30 minutes after the drug administration, they are also performed subcutaneous injection of ISO at a dose of 60 mg/kg; on the fourth day their tissue samples such as blood and heart are collected on the fourth day.

2. The acute myocardial ischemia model in rats with left anterior descending coronary artery ligation: SD rats are selected and divided into five groups: blank control group, model group, coptisine high dose group (100 mg/kg p.o.) and coptisine medium dose group 25 mg/kg p.o.), coptisine low dose group (10 mg/kg p.o.), with 10 rats in each group. The groups with drug administration are pre-administered drugs 24 h and 12 h in advance before the rats are anesthetized with 3% chloral hydrate at 10 ml/kg, laid flat on their backs and fixed on the rat plate. Then cut them open at between left 4th and 5th ribs to open the pericardium, expose the heart, gently press the thorax to extrude the heart, find the left anterior descending coronary artery in the pulmonary artery cone and left atrium, and immediately bind the root of the left anterior descending coronary artery (pulmonary artery cone and left atrial appendage) with suture 0; push the heart back to the chest, and squeeze out the blood and gas in the chest cavity, close the chest cavity quickly, suture the skin, and the chest opening time is no more than 30 s. Use the MPA200 biosignal analysis system to perform electrocardiogram on each rat. Collect blood samples such as blood and heart 24 hours after model is established.

3. Observation indicators and methods 3.1 Record ECG: Same as Embodiment 1.

3.2 Observing the pathological section of the heart: same as in Embodiment 1.

3.3 Method for determination of myocardial neuraminidase level: same as in Embodiment 1.

3.4 Detection method for serum myocardial damage index CK-MB and D-LDH: same as in Embodiment 1.

3.5 Determination of the inhibitory rate of coptisine on neuraminidase

Neuraminidase activity is determined using a neuraminidase assay kit. Accurately weigh standard coptisine, and prepare 200 μM (high dose group), 100 μM (medium dose group), and 50 μM (low dose group) solution in that order. To prepare a standard curve, add 70 μl of neuraminidase assay buffer to each well in a 96-well fluorescent plate, and add 0, 1, 2, 5, 7.5 and 10 μl of neuraminidase to each well, respectively. Then add 0-20 μl of Milli-Q water per well so the total volume of each well is 90 μl. To test the sample, add 70 μl of neuraminidase detection buffer to each well of a 96-well fluorescent plate, then add 10 μl of neuraminidase and 10 μl of coptisine solution in different concentrations per well. Add 0-10 μl of Milli-Q water per well so the total volume of each well is 90 After shaking for about 1 minute, incubate at 37° C. for 2 minutes so the inhibitor fully interacts with neuraminidase; then add 10 μl of neuraminidase fluorescein substrate per well, mix by shaking, incubate at 37° C. for 30 minutes and then perform fluorescence measurement at excitation wavelength 322 nm and emission wavelength of 450 nm.

III. Test Results

1. Impact on the ECG

The results of typical electrocardiogram show that after myocardial isoproterenol modeling, obvious myocardial damage is observed in the model group, and coptisine can effectively improve myocardial damage in a dose-dependent manner. The electrocardiogram of the high dose coptisine group is basically consistent with the blank control group.

2. Effect on Myocardial Cell Morphology

Typical cardiac pathological sections show that after myocardial isoproterenol modeling, the model group has showed obvious myocardial damage, which is manifested in irregular shape of cardiomyocytes, obvious intercellular fissures, and infiltration of inflammatory cells in a large number. Coptisine can effectively improve myocardial damage in a dose-dependent manner; the myocardial cell morphology and intercellular fissure in the high dose coptisine group are basically consistent with the blank control group, and there is no inflammatory cell infiltration.

3. Effect on the Expression Level of Myocardial Neuraminidase

After isoproterenol modeling, the expression of neuraminidase in rat cardiomyocytes is detected by ELISA. The results show that the expression of neuraminidase has been increased in the model group after myocardial ischemia (about 40%), and coptisine can effectively inhibit the increase of neuraminidase expression induced by myocardial ischemia in a dose-dependent manner (the low dose coptisine group has been reduced by about 21%); compared with the model group, the medium dose coptisine group has been reduced by about 29% and the high dose coptisine group has been reduced by about 40%).

4. Effect of Myocardial Damage Index on Serum Expression Level

CK-MB and D-LDH are serum markers of myocardial ischemic damage. After isoproterenol-induced acute myocardial ischemia modeling; serum CK-MB and LDH levels are increased, and the drug-administered groups have a significantly lower levels (low dose coptisine group has about 20% lower than that of the model group, the medium dose of coptisine is reduced by about 30% compared with the model group; the high dose coptisine group is reduced by about 40% compared with the model group).

5. Determination of the Inhibitory Rate of Coptisine on Neuraminidase

Table 3 shows the inhibitory rate of coptisine on neuraminidase, indicating that coptisine is a potent neuraminidase inhibitor, and its inhibitory rate on neuraminidase is concentration-dependent and its effect on myocardial ischemic damage may be related to its inhibition effect of neuraminidase.

TABLE 3

| Inhibitory rate of coptisine on neuraminidase | |
|---|---|
| Coptisine concentration (μM) | Inhibitory rate (%) |
| 50 | 5.64 |
| 100 | 28.69 |
| 200 | 56.25 |

Embodiment 3: Synergistic Improvement of Coptisine and Zanamivir or Oseltamivir on Myocardial Ischemic Damage Based on the Median-effect Principle, the dose-response relationship curve and the combined index curve (Fa-CI curve) under different effects have been drawn. The relationship chart of the two drugs is used to quantitatively evaluate if there is a synergy between the two drugs.

The combined index $CI=D_1/DX_1+D_2/DX_2+\alpha D_1D_2/DX_1DX_2$, where $DX_1$ and $DX_2$ are the concentrations of the two drugs when the two drugs are used alone, and when X effect is generated, and $D_1$ and $D_2$ are the required concentrations for the two drugs when the two drugs are combined and when X effect is generated. The mechanism of action of coptisine is the same as zanamivir and oseltamivir phosphate, by inhibiting the activity of neuraminidase, so $\alpha=1$. When CI<1, it indicates that the two drugs' combined use effect is synergistic; CI=1 indicates that the two drugs' combined use effect is additive; CI>1 indicates that the two drugs' combined use effect is antagonistic. According to the inhibitory rate on neuraminidase by single drug or combination of drugs, the dose-effect relationship curve is drawn, and then the combination index (CI) curve under different effects (Fa) is drawn.

By referring to the method described in "3.5 Determination of the inhibitory rate of coptisine on neuraminidase" in Embodiment 2, the inhibitory rates on neuraminidase by different concentrations of coptisine, zanamivir, and oseitamivir phosphate (sing drug) are measured, respectively, as well as the inhibitory rates on neuraminidase by combination of coptisine and zanamivir, coptisine and oseltamivir, and the dose-effect relationship curve is drawn, and then the combination index (CI) curve under different effects (Fa) is drawn. The effect analysis of combination of two drugs is as follows:

When coptisine is used in combination with zanamivir for neuraminidase, when Fa=0.40 (i.e. 40% neuraminidase is inhibited), CI≈1, the combined effect of the two drugs is synergistic. When Fa>0.40, CI>1, the combined effect of the two drugs is antagonistic. When Fa<0.40, CI<1, the combined effect of the two drugs is synergistic. The effect analysis of combined use of drugs has showed that there is a synergistic effect of coptisine and zanamivir on neuraminidase at low doses, which further suggests that the two can synergistically improve myocardial ischemic damage at low doses.

When coptisine is combined with oseltamivir phosphate for neuraminidase, when Fa=0.45 (i.e., 45% neuraminidase is inhibited), CI≈1, the combined effect of the two drugs is synergistic. When Fa>0.45, CI>1, the combined effect of the two drugs is antagonistic. When Fa<0.45, CI<1, the combined effect of the two drugs is synergistic. The effect analysis of combined use of drugs has showed that there is a synergistic effect between coptisine and oseltamivir phosphate at low dose on neuraminidase, which further suggests that the two can synergistically improve myocardial ischemic damage at low dose.

The effect analysis of combined use of two drugs has showed that a combination of coptisine and zanamivir or a combination of coptisine and oseltamivir for the treatment of myocardial ischemic damage can be developed. Due to the synergistic effect of coptisine and zanamivir or coptisine and oseltamivir phosphate at low doses, we can develop the combination of coptisine and zanamivir or the combination of coptisine and oseltamivir in a low dose form to improve the treatment of myocardial ischemic damage by repeated administration.

The above embodiments are intended to illustrate the substantial content of the present invention, but do not limit the scope of the present invention. A person skilled in the art should understand that the technical solutions of the present invention may be modified or equivalently substituted without departing from the spirit and protection scope of the present invention.

What is claimed is:

1. A method of preventing, alleviating, or treating myocardial ischemic damage in a subject, comprising: administering an effective amount of a pharmaceutical composition to the subject in need thereof;
   wherein the pharmaceutical composition contains a compound that inhibits the activity of neuraminidase; the myocardial ischemic damage is not influenza-associated; and the compound is oseltamivir phosphate.

* * * * *